(12) United States Patent
Tessmer

(10) Patent No.: US 10,098,723 B2
(45) Date of Patent: *Oct. 16, 2018

(54) NON-ENTANGLING VENA CAVA FILTER

(71) Applicant: C. R. BARD, INC., Murray Hill, NJ (US)

(72) Inventor: Alexander W. Tessmer, Phoenix, AZ (US)

(73) Assignee: C. R. BARD, INC., Murray Hill, NJ (US)

( * ) Notice: Subject to any disclaimer, the term of this patent is extended or adjusted under 35 U.S.C. 154(b) by 406 days.

This patent is subject to a terminal disclaimer.

(21) Appl. No.: 14/868,192

(22) Filed: Sep. 28, 2015

(65) Prior Publication Data

US 2016/0015506 A1 Jan. 21, 2016

Related U.S. Application Data

(60) Continuation of application No. 14/146,370, filed on Jan. 2, 2014, now Pat. No. 9,144,484, which is a continuation of application No. 13/688,031, filed on Nov. 28, 2012, now Pat. No. 8,628,556, which is a division of application No. 12/727,116, filed on Mar. 18, 2010, now Pat. No. 8,372,109, which is a continuation of application No. 10/912,601, filed on Aug. 4, 2004, now Pat. No. 7,704,267.

(51) Int. Cl.
*A61F 2/01* (2006.01)

(52) U.S. Cl.
CPC .......... *A61F 2/01* (2013.01); *A61F 2002/016* (2013.01); *A61F 2220/0016* (2013.01); *A61F 2230/005* (2013.01); *A61F 2230/008* (2013.01); *A61F 2230/0067* (2013.01); *A61F 2230/0093* (2013.01)

(58) Field of Classification Search
CPC ................ A61F 2/01; A61F 2220/0016; A61F 2230/0093; A61F 2230/0067; A61F 2230/008; A61F 2230/005; A61F 2002/016

See application file for complete search history.

(56) References Cited

U.S. PATENT DOCUMENTS

| | | | | |
|---|---|---|---|---|
| 5,147,379 A * | 9/1992 | Sabbaghian | ............. | A61F 2/01 606/108 |
| 5,903,927 A * | 5/1999 | Wolfe | .................... | A42B 1/004 2/209.13 |
| 7,704,267 B2 * | 4/2010 | Tessmer | .................... | A61F 2/01 606/200 |
| 8,628,556 B2 * | 1/2014 | Tessmer | .................... | A61F 2/01 606/200 |

(Continued)

*Primary Examiner* — Katherine M Shi
*Assistant Examiner* — Michael Mendoza
(74) *Attorney, Agent, or Firm* — Garvey, Smith & Nehrbass, Patent Attorneys, L.L.C.; Seth M. Nehrbass; Charles C. Garvey, Jr.

(57) ABSTRACT

A method of treating a patient includes providing an implantable vessel filter including a plurality of legs and center-post, inserting the filter into a delivery assembly, and deploying the filter at a desired location in a patient's body. One or more of the legs may have a hook at a distal end thereof and the center-post includes a grooved distal section to receive the hooks. The filter legs transition from a compressed configuration to an expanded configuration during deployment.

20 Claims, 4 Drawing Sheets

(56) References Cited

U.S. PATENT DOCUMENTS

| | | | | |
|---|---|---|---|---|
| 2003/0003871 A1* | 1/2003 | Urso | ............... | H04M 1/05 455/66.1 |
| 2004/0244096 A1* | 12/2004 | Claro | ............... | A42B 1/22 2/195.2 |
| 2012/0184985 A1* | 7/2012 | Ravenscroft | ............ | A61F 2/01 606/200 |

* cited by examiner

NON-ENTANGLING VENA CAVA FILTER

PRIORITY

This application is a continuation of U.S. patent application Ser. No. 14/146,370, filed Jan. 2, 2014, now U.S. Pat. No. 9,144,484, which is a continuation of U.S. patent application Ser. No. 13/688,031, filed Nov. 28, 2012, now U.S. Pat. No. 8,628,556, which is a division of U.S. patent application Ser. No. 12/727,116, filed Mar. 18, 2010, now U.S. Pat. No. 8,372,109, which is a continuation of U.S. patent application Ser. No. 10/912,601, filed Aug. 4, 2004, now U.S. Pat. No. 7,704,267, each of which is incorporated by reference in its entirety herein.

BACKGROUND OF THE INVENTION

A vena cava filter is a device inserted into a blood vessel to capture particles in the blood flow. Typically the device is inserted into a major vein to prevent a blood clot from reaching the lungs. Patients who have recently suffered from trauma, heart attack (myocardial infarction), or underwent major surgical procedure (e.g., surgical repair of a fractured hip, etc.) may have thrombosis in a deep vein. When the thrombus clot loosens from the site of formation and travels to the lung it may cause pulmonary embolism, a life-threatening condition. A vena cava filter may be placed in the circulatory system to intercept the thrombi and prevent them from entering the lungs.

Examples of various blood vessel filters are disclosed in U.S. Patent Application Publication No. 2001/0000799 A1, titled "BODY VESSEL FILTER" by Wessman et al., published May 3, 2001; U.S. Patent Application Publication No. 2002/0038097 A1, titled "ATRAUMATIC ANCHORING AND DISENGAGEMENT MECHANISM FOR PERMANENT IMPLANT DEVICE" by Ostrovsky et al., published Sep. 26, 2002; U.S. Patent Application Publication No. 2002/0193828 A1, titled "ENDOVASCULAR FILTER" by Griffin et al., published Dec. 19, 2002; U.S. Patent Application Publication No. 2003/0199918 A1, titled "CONVERTIBLE BLOOD CLOT FILTER" by Patel et al., published Oct. 23, 2003; U.S. Patent Application Publication No. 2003/0208227 A1, titled "TEMPORARY VASCULAR FILTERS AND METHODS" by Thomas, published Nov. 6, 2003; U.S. Patent Application Publication No. 2003/0208253 A1, titled "BLOOD CLOT FILTER" by Beyer et al., published Nov. 6, 2003; U.S. Pat. No. 4,425,908, titled "BLOOD CLOT FILTER" issued to Simon, dated Jan. 17, 1984; U.S. Pat. No. 4,643,184, titled "EMBOLUS TRAP" issued to Mobin-Uddin, dated Feb. 17, 1987; U.S. Pat. No. 4,817,600, titled "IMPLANTABLE FILTER" issued to Herms et al., dated Apr. 4, 1989; U.S. Pat. No. 5,059,205, titled "PERCUTANEOUS ANTI-MIGRATION VENA CAVA FILTER" issued to El-Nounou et al., dated Oct. 22, 1991; U.S. Pat. No. 5,626,605, entitled "THROMBOSIS FILTER" issued to Irie et al., dated May 6, 1997; U.S. Pat. No. 5,755,790, titled "INTRALUMINAL MEDICAL DEVICE" issued to Chevillon et al., dated May 26, 1998; U.S. Pat. No. 6,258,026 B1, titled "REMOVABLE EMBOLUS BLOOD CLOT FILTER AND FILTER DELIVERY UNIT" issued to Ravenscroft et al., dated Jul. 10, 2001; U.S. Pat. No. 6,497,709 B1, titled "METAL MEDICAL DEVICE" issued to Heath, dated Dec. 24, 2002; U.S. Pat. No. 6,506,205 B2, titled "BLOOD CLOT FILTERING SYSTEM issued to Goldberg et al., dated Jan. 14, 2003; and U.S. Pat. No. 6,517,559 B1, titled "BLOOD FILTER AND METHOD FOR TREATING VASCULAR DISEASE" issued to O'Connell, dated Feb. 11, 2003; U.S. Pat. No. 6,540,767 B1, titled "RECOILABLE THROMBOSIS FILTERING DEVICE AND METHOD" issued to Walak et al., dated Apr. 1, 2003; U.S. Pat. No. 6,620,183 B2, titled "THROMBUS FILTER WITH BREAK-AWAY ANCHOR MEMBERS" issued to DiMatteo, dated Sep. 16, 2003; each of which is incorporated herein by reference in its entirety.

Typically the filter comprises a plurality of radially expandable legs that supports one or more filter baskets which are conical in configuration. The device is adapted for compression into a small size to facilitate delivery into a vascular passageway and is subsequently expandable into contact with the inner wall of the vessel. The device may later be retrieved from the deployed site by compressing the radially expanded legs and the associated baskets back into a small size for retrieval. The radially expandable leg may further comprise engagements for anchoring the filter in position within a blood vessel (e.g., vena cava). For example, the expandable legs may have hooks that can penetrate into the vessel wall and positively prevent migration of the filter in either direction along the length of the vessel. The body of the filter may comprise various biocompatible materials including compressible spring metals and shape memory materials to allow easy expansion and compression of the filter within the vessel. The hooks on the radially expandable legs may further comprise materials more elastic than the legs to permit the hooks to straighten in response to withdrawal forces to facilitate withdrawal from the endothelium layer without risk of significant injury to the vessel wall. In one variation, the hooks are formed on the ends of a portion of the radially expandable legs, but not on others.

Many of the existing vena cava filters routinely encounter problems during deployment due to entanglements of the radially expandable legs. This is especially problematic in designs with hooks implemented on the radially expandable legs. In the compressed/collapsed condition, the various hooks on the legs may interlock with other legs or hooks and render the device useless. Thus, an improved filter design that can prevent entanglement and/or interlocking of the radially expandable legs may be desirable. Such a design may improve the reliability of the vena cava filter and improve the surgical success rate of filter implantation. Such an improved design may also prevent the entanglement of the radially expandable legs when the device is collapsed into the compressed position during the retrieval of the filter from its deployed location within the vessel.

BRIEF SUMMARY OF THE INVENTION

Accordingly, described herein is an implantable vessel filter with a center-post configured to prevent entanglement of the filter's radially expandable legs. This improved vessel filter may prevent the radially expandable legs from entanglement and may further prevent the hooks on the radially expandable legs from interlocking In one variation, the implantable vessel filter comprises a plurality of radially expandable elongated legs forming at least one conical-shaped filter when placed in the expanded position. A center-post is provided along the longitudinal axis of the filter to prevent the legs from entangling when the legs are collapsed inward toward the longitudinal axis of the filter. The center-post is configured to separate the legs and/or the associated hooks in the collapsed position. Surface profiles such as grooves or ledges may be provided on the center-post to separate the legs and/or hooks from each other. In one particular design, the distal portion of the center-post is configured with a plurality of cavities on the circumferential surface for receiving the hooks located at the proximal end of the radially expandable legs.

In another variation, the implantable vessel filter comprises a sleeve at the proximal end of the device and a plurality of elongated legs extending from the sleeve towards the distal direction. The legs are radially expandable. In the expanded position, a first set of the legs forms a first conical-shaped filter basket, and a second set of the legs forms a second conical-shaped filter basket distal to the first basket. As least three of the legs from the second set of the legs have hooks on them for anchoring into the vessel wall. Preferably, the hooks are located at the distal end of the legs. The implantable vessel filter further comprises a center-post connected to the sleeve and positioned along the longitudinal axis of the filter. The center-post is configured to prevent the legs from crossing the longitudinal axis so that the various legs do not entangle with each other and the hooks do not interlock. Preferably, grooves are provided on the circumferential surface of the center-post to further maintain the separation of the hooks when the legs are placed in the compressed position.

The improved implantable vessel filter may provide one or more of the various advantages listed below: improved loading into the delivery system; improved deployability due to easier release of the radially expandable legs; improved retrievability due to prevention of leg entanglement when the legs are collapsed inward for removal from the deployed site; trapping of significant emboli; good vessel patency and limited thrombogenic response at the implantation site; minimal migration along the length of the vessel after implantation; no perforation of the vessel wall; low profile for easy insertion; high durability, fatigue resistance and biocompatibility.

These and other embodiments, features and advantages of the present invention will become more apparent to those skilled in the art when taken with reference to the following more detailed description of the invention in conjunction with the accompanying drawings that are first briefly described.

DETAILED DESCRIPTION OF THE INVENTION

The following detailed description should be read with reference to the drawings, m which like elements in different drawings are identically numbered. The drawings, which are not necessarily to scale, depict selected preferred embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Before describing the present invention, it is to be understood that unless otherwise indicated this invention need not be limited to applications in humans. As one of ordinary skill in the art would appreciate, variations of the invention may be applied to other mammals as well. Moreover, it should be understood that embodiments of the present invention may be applied in combination with various catheters, tubing introducers or other filter deployment devices for implantation and/or retrieval of the filter in a vessel within a patient's body.

A vena cava filter is used herein as an example application of the filter device to illustrate the various aspects of the invention disclosed herein. In light of the disclosure herein, one of ordinary skill in the art would appreciate that variations of the filter device may be applicable for placement in various blood vessels, hollow body organs or elongated cavities in a human body for capturing particles in a fluid stream. It is also contemplated that the filter device described herein may be implemented for capturing particles other than blood clots.

It must also be noted that, as used in this specification and the appended claims, the singular forms "a," "an" and "the" include plural referents unless the context clearly dictates otherwise. Thus, for example, the term "a hook" is intended to mean a single hook or a combination of hooks, "a fluid" is intended to mean one or more fluids, or a mixture thereof.

Figure 1A:
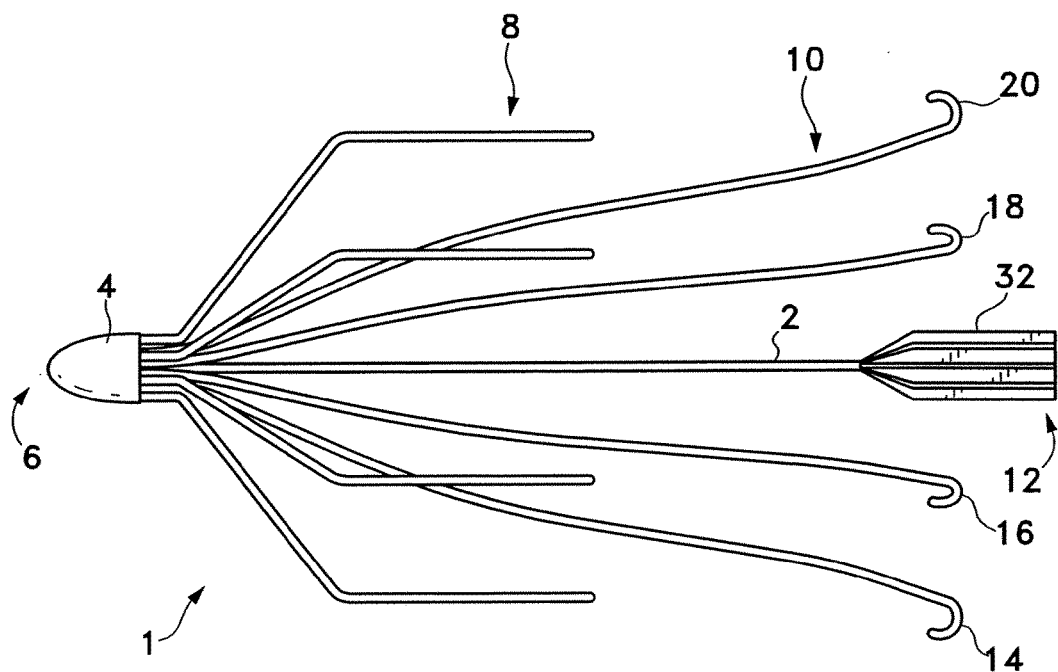
FIG. 1A illustrates one variation of an implantable vessel filter with a center-post for preventing entanglements of the radially expandable legs.
Figure 1B:
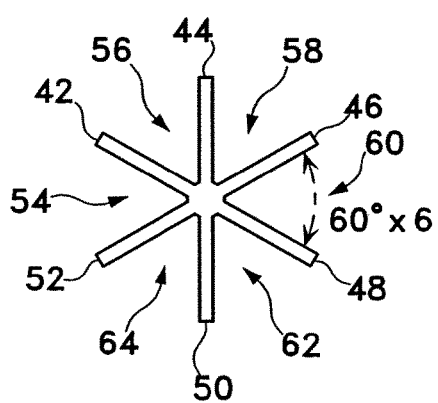
FIG. 1B shows the top view of the center-post of the implantable vessel filter of FIG. 1A. Flanges are provided at the distal end of the center-post, protruding in the radial direction, for separating the hooks at the distal end of the radially expandable legs.
Figure 1C:
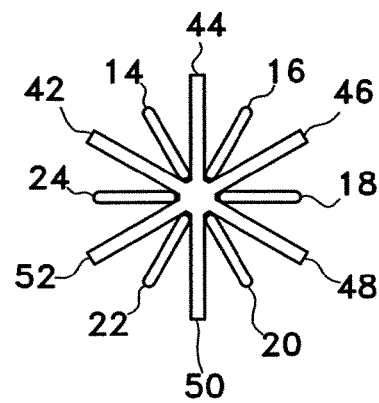
FIG. 1C is a diagram illustrating the placement of the hooks in between the flanges at the distal end of the center-post. In this particular variation, the height of the hooks is less than the height of the flanges in the radial direction from the center of the post, such that the flanges may prevent the hooks from tearing the inner walls of the vessel in the compressed position.

In one aspect of the invention, the implantable vessel filter 1 comprises an elongated body acting as the center-post 2 of the device, as shown in FIG. 1A. A sleeve 4 is connected to the proximal end of the center-post. The proximal end 6 of the sleeve 4 may be tapered to provide a bullet-shaped profile to facilitate the insertion and/or retrieval of the device in a vessel. A plurality of legs 8, 10 (e.g., flexible or semi-flexible wiring, etc.) extending from the sleeve 4 in the radial direction towards the distal end 12 of the device. The legs 8, 10 are configured with materials such that they may be collapsed toward the center-post 2 and positioned along the length of the center-post 2 for insertion and/or retrieval from a patient's vascular system. The plurality of legs comprises two sets of legs 8, 10. A first set of six legs 8, when expanded, forms a first conical-shaped filter basket centered around the center-post 2, which is on the longitudinal axis of the device 1. A second set of six legs 10, when expanded, forms a second conical-shaped filter basket positioned distal to the first basket, which is also centered around the center-post 2. Hooks 14, 16, 18, 20 are provided at the distal ends of the second set of legs 10 for anchoring the distal end of the second set of legs 10 into the walls of the vessel. An attachment 32 is provided at the distal end of the device for separating the hooks and preventing the hooks from interlocking with each other. Optionally, the attachment 32 comprises a plurality of flanges protruding in the radial direction from the center-post. In one design variation, the flanges 42, 44, 46, 48, 50, 52 are spaced equally around the circumferential surface of the attachment with spacing approximately 60 degrees apart, as shown in FIG. 1B. Each of the slots 54, 56, 58, 60, 62, 64 between the flanges 42, 44, 46, 48, 50, 52 may be configured to receive one hook. The height of the flanges 42, 44, 46, 48, 50, 52 may be configured to be greater than the height of the hooks 14, 16, 18, 20, 22, 24 in the radial direction, such that the tip of the hooks does not extend beyond the flanges when placed in the compressed position, as illustrated in FIG. 1C. This may prevent the tip of the hooks from accidentally tearing the wall of the vessel and allow smoother deployment and/or retrieval of the implantable vessel filter device.

In addition, the distal end of the center-post may be configured for attachment to a deployment device (e.g., introducer). For example, interlocking mechanisms matching the adaptor at an end of a deployment device may be provided to secure the implantable vessel filter to the tip of the deployment device for delivery and/or deployment. In another variation, the attachment positioned at the distal end of the center-post may be configured to serve dual functions such that the circumferential surface along the length of the attachment is configured with grooves for receiving and separating the hooks, while the distal end of the attachment is configured for interfacing with a deployment device. The grooves may be configured as indentations, cavities, raised surface profiles such as flanges, and other changes in surface profile. Alternatively, the proximal end of the attachment may be configured with an interface (e.g., hook, loop, etc.) for interconnecting with a deployment device to facilitate deployment and/or retrieval of the implantable vessel filter.

In another variation, the device is configured such that in the compressed position the center-post extends distally beyond the length of the legs. At the distal end of the extended center-post, one may provide an interface or interlocking mechanism (e.g., hook, loop, etc.) for interconnecting with a deployment/retrieval device.

In yet another design variation, the center-post extends beyond proximal end of the sleeve and protrudes at the proximal end of the filter. The proximal end of the center-post may be configured with an interface or interlocking mechanism (e.g., hook, loop, etc.) for interconnecting with a filter deployment/retrieval device to facilitate deployment and/or retrieval of the implantable vessel filter.

Although in the example discuss above, the plurality of legs forms two filter baskets along the longitudinal length of the device. One may configure the device with only one filter basket, or alternatively with three or more filter baskets. In addition, the device may be configured with three or more legs forming each basket and is not limited to the six-legged basket as shown above. Also discussed earlier, barb feet (e.g., hooks) may be provided on the distal end of each leg. As one of ordinary skill in the art would appreciate, the precise length and angle of the barb feet may be designed to provide secure attachment to the vessel wall without causing perforation or tearing. Moreover, hooks may be provided on all the distal legs or only on some of the distal legs. Hooks may also be provided on the proximal legs if desired. Furthermore, secondary struts may be provided for interconnecting two or more of the radially expandable legs. The secondary struts may increase wiring density for each filter basket, which may in turn increase the filters capability to capture smaller particles.

The sleeve may be comprised of biocompatible metal, metal alloyed, or polymeric materials. The legs may be comprised of metal (e.g., stainless steel, titanium, etc.), metal alloyed (e.g., titanium alloy, elgiloy, an alloy comprises Cobalt-Nickel-Chromium, etc.), shape memory material (e.g., Nitinol), or polymeric materials (e.g., biocompatible plastics, etc.). The center-post may be comprised of metal, metal alloyed, polymeric materials or a combination thereof. For example, the center-post may be comprised of a metal alloyed core with polymeric coating on the outside. The grooves on the center-post for receiving the legs and/or the hooks may be an integral part of the shaft of the center-post, or they may be provided through an attachment connected to the center-post. The attachment may be comprised of metal, metal alloyed, polymeric material or a combination thereof.

Figure 2:
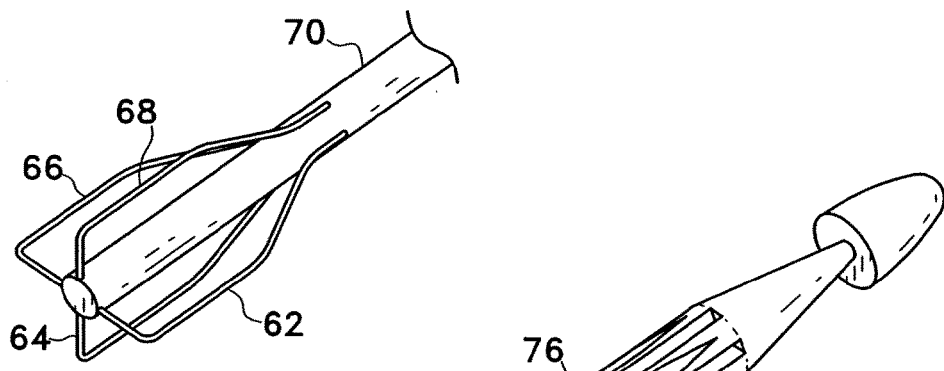
FIG. 2 illustrates another variation of the device where the wirings extending from the center-post provide the medium for separating the legs of the implantable vessel filter.
Figure 3:
FIG. 3 illustrates yet another variation where the center-post has embedded grooves for receiving the radially expandable legs of the implantable vessel filter. In this variation, two sets of grooves are provided, with one set of grooves for receiving a first set of legs which forms the proximal filter basket, and a second set of grooves for receiving a second set of legs which forms the distal filter basket. The corresponding radially expandable legs are omitted in this particular figure.

In another variation, as shown in FIG. 2, the flanges 62, 64, 66, 68 at the distal portion of the center-post comprise wirings extending from the shaft 70 of the center-post. The looped wiring provides the medium to separate the hooks, while allowing fluid to flow through the center of the loops to minimize disruption of blood flow along the length of the device. In yet another variation, grooves or cavities are provided along the shaft of the center-post 2 for receiving the legs and/or the hooks. In one design, grooves are provided at the distal portion 72 of the shaft to receive the distal legs, with a hook at the distal end of each distal leg. In another design, the grooves are provided to receive all the legs of the device. In one variation, shown in FIG. 3, a first set of grooves 76 positioned along a proximal portion 74 of the shaft of the center-post 2 is provided to receive a first set of legs which forms a proximal filter basket, and a second set of grooves 78 positioned along the length of the shaft is provided to receive a second set of legs which form the distal filter basket. In FIG. 3, the filter device is shown without its corresponding radially expandable legs.

Figure 4:
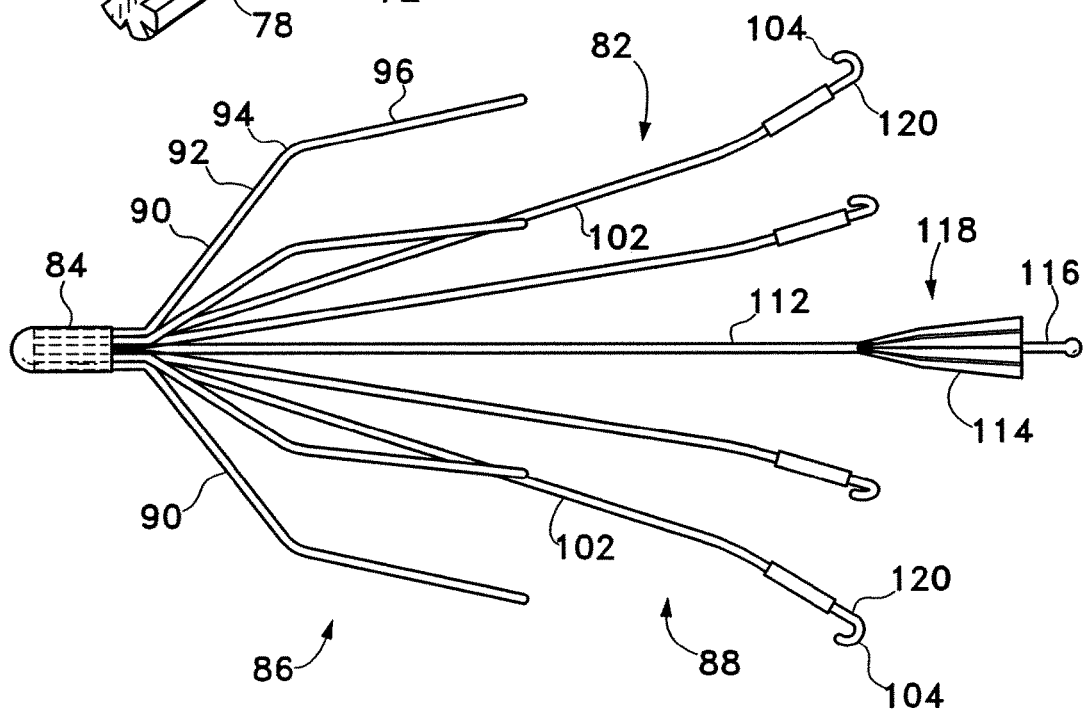
FIG. 4 is a diagrammatic view of another variation of an implantable vessel filter.

Referring now to FIG. 4, an expanded implantable vessel filter 82 is illustrated which is made from sets of elongate metal wires. In this variation, the wires are held together at the filter's proximal end by a hub 84 where they are plasma welded together to the hub or otherwise joined. In the low temperature martensite phase of wires made of thermal shape memory material (e.g., Nitinol alloy), the sets of wires can be straightened and held in a straight form that can pass through a length of fine plastic tubing with an internal diameter of approximately 2 mm (e.g., 8 French catheter). In its high temperature austenitic form, the vessel filter 82 recovers a preformed filtering shape as illustrated by FIG. 4. Similarly, wires of spring metal can be straightened and compressed within a catheter or tube and will diverge into the filter shape of FIG. 4 when the tube is removed.

In its normal expanded configuration or preformed filtering shape, the vessel filter 82 comprises a double filter, having a first proximally positioned basket section 86 and a second distally disposed filter basket section 88. The two filter basket sections provide peripheral portions which can both engage the inner wall of a body vessel at two longitudinally spaced locations, and the two filter basket sections are generally symmetrical about a longitudinal axis passing through the hub 84. On the other hand, the first filter basket section 86, which may act as a centering unit, may not always touch the vessel wall on all sides.

The first filter basket section 86 is formed from short lengths of wire, which form legs 90 that extend angularly, outwardly and then downwardly away from the hub 84 and towards the distal end of the vessel filter 82. Each leg 90 has a first leg section 92 which extends angularly outwardly from the hub 84 to a transition section 94, and an outer leg section 92 extends angularly from the transition section 94 toward the distal direction of the filter. The outer leg sections 96 are substantially straight lengths with ends which lie on a circle at their maximum divergence and engage the wall of a vessel at a slight angle (preferably within a range of from ten to forty-five degrees) to center the hub 84 within the vessel. For a filter which is to be removed by grasping the hub 84, it may be important for the hub to be centered. The filter may be configured with six wires 90 of equal length extending radially outward from the hub 84 and circumferentially spaced, such as, for example, by sixty degrees of arc.

The second filter basket section 88 is the primary filter and can include up to twelve circumferentially spaced straight wires 102 forming downwardly extending legs which tilt outwardly of the longitudinal axis of the filter 82 from the hub 84. A filter with a six wire configuration is discussed in this example, and the wires are of equal length. Alternatively, the length of the wiring may be staggered. The wires 102 are preferably much longer than the wires 90, and have distal tip sections which are uniquely formed, outwardly oriented hooks 104 which lie on a circle at the maximum divergence of the wires 102. There may be from three to twelve wires 102 formed with hooks 104, and in some instances, the wire legs 90 may include similarly formed hooks at the free ends thereof. The wires 102, in their expanded configuration of FIG. 4, are at a slight angle to the vessel wall, preferably within a range of from ten to forty-five degrees, while the hooks 104 penetrate the vessel wall to anchor the filter against movement. The wires 102 are radially offset relative to the wires 90 and may be positioned halfway between the wires 90 and also may be circumferentially spaced by sixty degrees of arc. Thus, the combined filter basket sections 86 and 88 can provide a wire positioned at every thirty degrees of arc at the maximum divergence of the filter sections. The filter section 88 forms a concave filter basket opening toward the distal end of the filter 82 while the filter section 86 forms a concave filter proximal of the filter section 88.

The vessel filter further comprises a center-post 112 positioned along the longitudinal axis of the filter with the proximal end of the center-post 112 connected to the hub 84. At the distal portion of the center-post, a raised surface profile 114 provides grooves for receiving the hooks 104 on the distal end of the distal legs 102. Preferably, each of the hooks 104 is provided with a corresponding groove on the shaft of the center-post 112. Alternatively, the grooves may be proved on the shaft to receive a portion of the distal leg 102 instead of the hook 104, thereby keeping the distal legs 102 from entangling with each other. In addition, the center-post 112 may have distal section 116 extending beyond the hook interface region 118. The extended distal section 116 may be configured to facilitate the handling of the vessel filter for pre-deployment preparation, deployment or extraction.

Furthermore, the hooks 114 on the distal legs may be further configured such that withdrawal force to which the hook is subjected will cause flexure in the juncture sections 120 so that the hook extends in the distal direction of the filter to a position parallel or semi-parallel with the axis of the leg 102. For example, the juncture section 120 may have considerably reduced cross-section relative to the cross-section of the leg 102 and the remainder of the hook 104 so that the stress exerted by the withdrawal tension may force it to bend outward. With the hook so straightened, it can be withdrawn without tearing the vessel wall, leaving only a small puncture. In an alternative design, the entire hook 104 can be formed with a cross-section throughout its length which is less than that of the leg 102. This may result in straightening of the hook over its entire length in response to a withdrawal force. This elasticity in the hook structure may prevent the hook from tearing the vessel wall during withdrawal.

Figure 5:
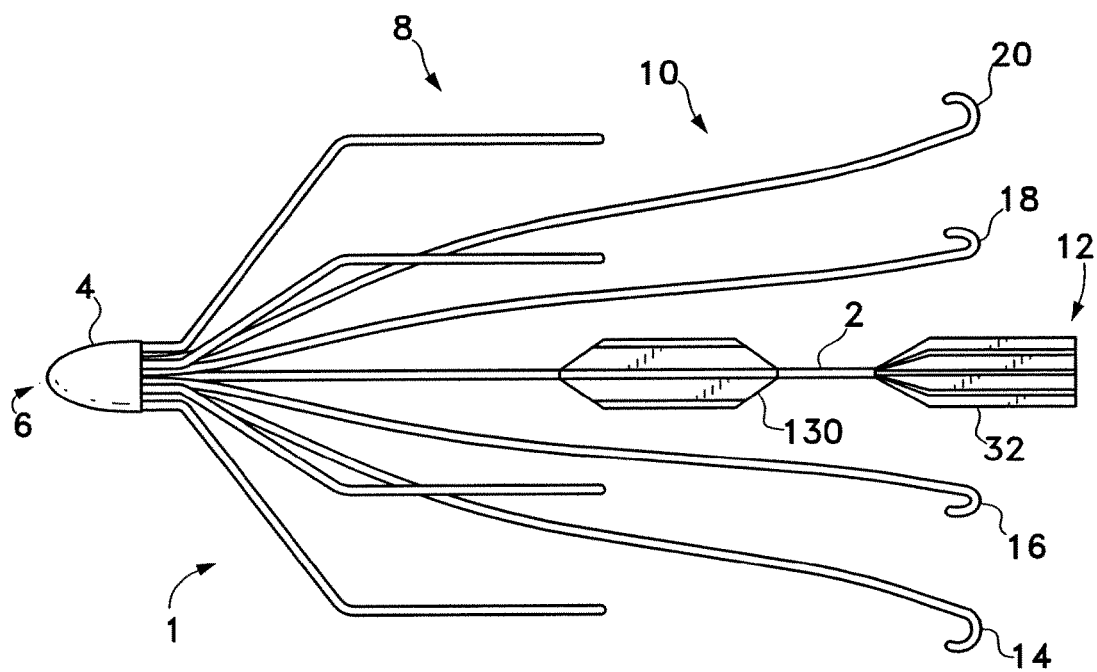
FIG. 5 illustrates another variation where two attachments are provided on the center-post for receiving the legs. In this particular variation, a first attachment is provided at the distal end to receive the hooks from the distal legs, and a second attachment is provided along mid-shaft of the center-post for receiving the proximal legs.

In another design, the vessel filter comprises two or more sets of grooves positioned along the length of the center-post for receiving the legs and/or hooks. The different sets of grooves may be provided on two or more attachments, with each attachment supporting one set of grooves. In one example, shown in FIG. 5, two attachments 32, 130 are provided along the length of the center-post 2 for receiving the legs 8, 10. A first attachment 32 is positioned at the distal end 12 of the center-post 2 for receiving the hooks 14, 16, 18, 20 from the distal legs 10. The hooks 14, 16, 18, 20 may be in a curved configuration when they are placed into the grooves on the attachment. Alternatively, the hooks 14, 16, 18, 20 may be straightened before they are placed within the grooves. A second attachment 130 is positioned along the mid-section of the center-post 2 and configured to receive the proximal legs 8. In this variation, each of the legs has a corresponding groove for receiving that leg.

Although it is preferable that each groove is designed for receiving a corresponding leg, one may also design an attachment or surface profile on the center-post with a plurality of grooves that are not pre-assigned to specific legs, such that when the legs are compressed, the legs would naturally fall into one of the convenient grooves. Preferably, each of the groove is design to receive one leg/hook, so that once a groove is filled by a leg, it would prevent a second leg from entering the same groove and forcing the second leg to go into an nearby groove.

Figure 6A:
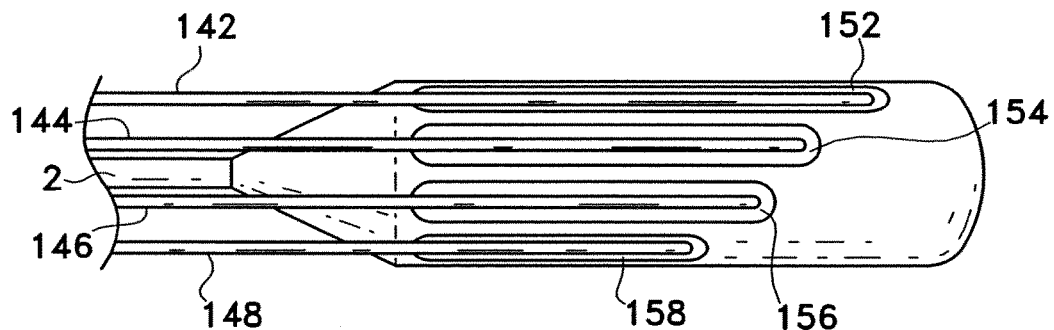
FIG. 6A illustrates another variation where the receiving slots are provided on the center-post for receiving the legs and/or hooks when the device is compressed. In this variation, the slots are configured in a step-wise manner and in a helical pattern around the circumferential surface of the center-post. The corresponding legs are also configured with varying lengths that decrease in a step-wise manner in the circumferential direction.

In yet another design, the legs of the vessel filter may have varying lengths and corresponding groves are provided on the center-post to receive the legs. In one variation, the legs 142, 144, 146, 148 with hooks are provided in a step-wise configuration forming a helical pattern along the circumferential direction around the center-post 2, as shown in FIG. 6A. Slots/grooves 152, 154, 156, 158 are provided on the center-post 2 where each of the slots has a length that matches the extension of the corresponding leg. The slots may be configured to receive the legs with their hooks in the curved position. Alternatively, the slots may be configured to receive the legs with their hooks straightened out. It is also contemplated that the slots/grooves may be configured to receive the legs with the hooks in either curved or straightened position.

Figure 6B:
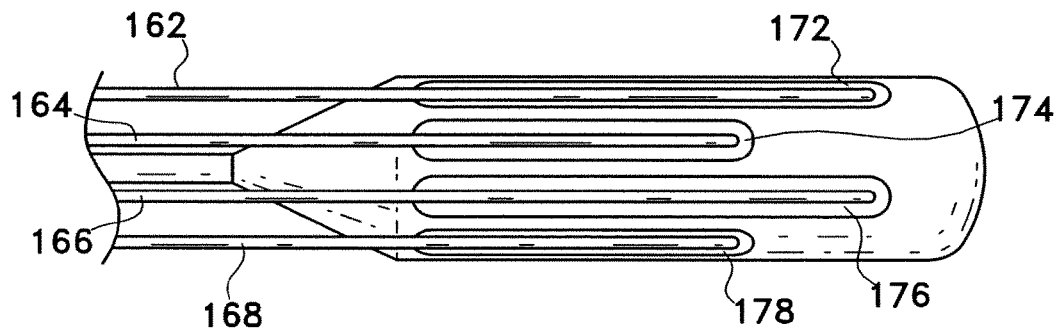
FIG. 6B illustrates yet another variation where the receiving slots are provided on the center-post for receiving the legs and/or hooks when the device is compressed. In this variation, the slots are configured in a staggered fashion and the corresponding legs comprise of legs of two different lengths forming a staggered pattern around the center-post.

In another variation, the length of the distal legs 162, 164, 166, 168 are staggered with one set of legs 162, 166 longer than the other set of legs 164, 168, as shown in FIG. 6B. In this particular configuration each of the short legs are place in between two long legs. Slots 172, 174, 176, 178 corresponding to the staggered legs are provided on the shaft of the center-post 2 for receiving the distal portion of each of the legs 162, 164, 1666, 168. As discussed earlier, depending on the particular design of the hook mechanism, the hook on each of the legs may be in a curved position or a straight position when compressed onto the center-post.

Figures 7A, 7B:
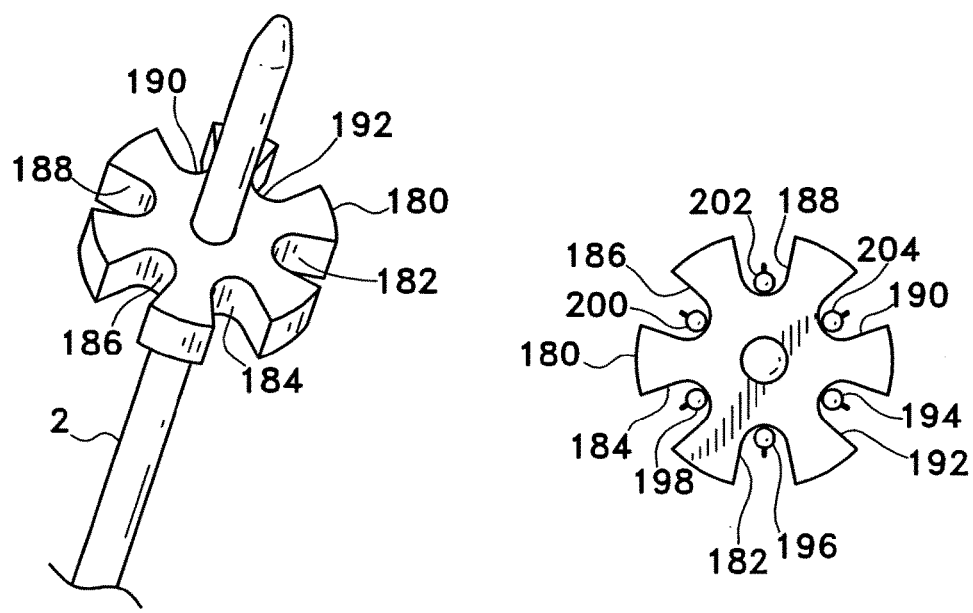
FIG. 7A illustrates another variation where the attachment for receiving the legs and/or hooks comprises a disk positioned on the center-post. The disk has slots/grooves for receiving the legs and separating the hooks from each other. The disk is shown without the corresponding legs.
FIG. 7B shows a top view of the center-post with the disk from FIG. 7A. In this figure the disk is shown with the corresponding legs positioned within the grooves on the disk.

In another design, a disk 180 is provided on the center-post 2 for receiving the legs and/or hooks when the legs are compressed. FIG. 7A illustrates one variation where a disk 180 is positioned at the distal portion of the center-post 2. The periphery of the disk is configured with grooves/slots 182, 184, 186, 188, 190, 192 for receiving the legs of the vessel filter when the legs are compressed toward the center-post 2. In the variation shown in FIG. 7A, one disk 180 is provided at the distal portion of the center-post 2, and the center-post 2 protrude from the disk 180 and extends distally, as shown in FIG. 7A. Alternatively, the disk may be placed at the distal end of the center-post. FIG. 7B illustrates the position of the corresponding legs 194, 196, 198, 200, 202, 204 when they are placed within the grooves 182, 184, 186, 188, 190, 192 on the disk 180. The center-post may be configured with one, two or more disk. In another variation, two disks are provided along the length of the center-post. A disk is provided at the distal portion of the center-post for receiving the distal legs by capturing each of the legs at its distal portion or distal end. A second disk is provided at the mid-shaft, and it is configured with one set of grooves for receiving the distal legs (capturing each leg at its mid-section), and a second set of grooves for receiving the proximal legs.

The implantable vessel filter disclosed herein may be inserted in various vessels throughout the human body. Two common applications are (1) insertion through the right or left femoral artery for placement within the inferior vena cava, and (2) insertion into the jugular vein at the neck, also for placement at the inferior vena cava. In one example, the implantable vessel filter is prepared by collapsing the legs of the filter onto the center-post and making sure that the each of the hooks are aligned with its corresponding grooves/cavities on the center-post. The compressed vessel filter is then placed into a delivery assembly with the filter hooks close to the distal opening of the delivery assembly (i.e., the distal end of the vessel filter aligned towards distal end of the delivery assembly). The surgeon first locates a suitable jugular or subclavian vein. An incision is made to access the vein. A guide-wire is inserted into the vein and advanced towards the inferior vena cava. An introducer sheath together with its tapered dilator is advanced over the guide-wire, and the distal portion of the introducer sheath is advanced into the inferior vena cava. The guide-wire and the dilator are then removed leaving the introducer sheath with its tip in the inferior vena cava. Venacavavogram or other imaging techniques may be used to position the introducer sheath for optimal placement of the vessel filter. The delivery assembly loaded with the vessel filter is then inserted into the introducer sheath and advanced towards the inferior vena cava. Once the delivery assembly in positioned for desired placement of the vessel filter, the surgeon may then pull back on the introducer hub to retract both the introducer sheath and the delivery assembly. The pusher pad inside of the delivery assembly will force the vessel filter to exit the delivery assembly and release the filter's legs. The delivery assembly and the introducer sheath may then be removed.

In another example, the vessel filter is inserted through the femoral artery. A guide-wire is inserted through the femoral artery and advanced toward the inferior vena cava. Once the guide-wire is in place, an introducer catheter together with its tapered dilator is inserted over the guide-wire. The introducer catheter is advanced toward the inferior vena cava and positioned just below the renal veins. The guide-wire and the dilator are then removed, leaving the introducer catheter with its distal tip in the inferior vena cava. A filter storage tube, which holds the vessel filter with its legs compressed on the center-post grooves, is then attached directly to the proximal end of the introducer catheter. A pusher wire is then used to push the vessel filter into the introducer catheter with the proximal end of the vessel filter in the forward advancing direction and the pusher wire pushing on the distal end of the vessel filter. The surgeon may then continuously advance the filter toward the distal end of the introducer catheter by pushing and forwarding the pusher wire. Once the proximal end of the filter reaches the distal end of the introducer catheter, the surgeon may stop the advancement of the filter. Holding the pusher wire stationary, the surgeon may then withdraw the introducer catheter and release the vessel filter allowing the legs of the filter to expand radially. The introducer catheter and the pusher wire are then withdrawn from the patient's body.

To remove the deployed filter, one may insert an introducer catheter, with the assistance of a guide-wire and a tapered dilator, into the jugular vein and advance the introducer catheter down to the position of the deployed vessel filter. A recovery cone is inserted into the introducer catheter and advanced towards the distal end of the introducer catheter by moving a pusher shaft forward into the introducer catheter. Once the recover cone reaches the distal end of the introducer catheter, the introducer catheter is unsheathed to open the recovery cone. The recovery cone is then advanced forward and over the filter tip by advancing the pusher shaft. One may then close the recovery cone over the filter tip by advancing the introducer catheter over the cone while holding the pusher shaft stationary. The closing of the recovery cone forces the legs of the vessel filter to collapsed onto the shaft of the center-post while forcing the hooks on each of the legs into their corresponding grooves on the shaft of the center-post. The vessel filter is then drawn into the lumen of the introducer catheter, and the introducer catheter along with the vessel filter is then withdrawn from the body of the patient.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

The invention claimed is:

1. An implantable vessel filter comprising:
   a hub;
   an elongate body including a grooved distal section and a center-post; wherein the elongate body proximally couples to the hub;
   a plurality of legs wherein at least some of the legs comprise a distally located hook;
   wherein
   the filter is operable between a filter-collapsed configuration and a filter-expanded configuration;
   in the filter-expanded configuration the plurality of legs extends radially outward from the center-post and the hooks penetrate a vessel wall;
   and
   in the filter-compressed configuration the plurality of legs are collapsed and the hooks lie in the groove.

2. The filter of claim 1 wherein the grooved distal section comprises a plurality of flanges extending radially outward from the distal section and a plurality of slots between the flanges.

3. The filter of claim 2 wherein the flanges are evenly spaced around a circumferential surface of the elongated body.

4. The filter of claim 3 wherein the plurality of legs has
   a first leg group comprising legs extending angularly outward from the hub in the filter-expanded configuration
   and
   a second leg group comprising legs extending angularly from the first leg group toward the grooved distal section.

5. The filter of claim 4 wherein the second leg group legs are substantially straight.

6. The filter of claim 5 wherein the plurality of legs comprise a shape memory metal.

7. The filter of claim 6 wherein each hook is formed with a maximum migration resistance force such that a proximal withdrawal force applied to the hook that is in excess of the filter maximum migration resistance force will cause the hook to straighten and bend toward a filter longitudinal axis.

8. The filter of claim 7 wherein the hub comprises a retrieval interlocking mechanism.

9. The filter of claim 8 wherein the retrieval interlocking mechanism is a retrieval hook.

10. The filter of claim 9 wherein a distal end of the elongated body extends beyond the distal ends of each of the second leg group legs in the filter-compressed configuration.

11. The filter of claim 10 further comprising a hook positioned at the distal end of the elongated body.

12. The filter of claim 11 wherein
    the second leg group comprises six legs,
    and
    the distal section includes six flanges configured to separate the hooks on the distal end of the second leg group legs in the filter-compressed configuration
    and
    the flanges lie approximately equidistant from each other.

13. The filter of claim 4 wherein each hook is formed with a maximum migration resistance force such that a proximal withdrawal force applied to the hook that is in excess of the filter maximum migration resistance force will cause the hook to straighten and bend toward a filter longitudinal axis.

14. The filter of claim 13 wherein the hub comprises a retrieval interlocking mechanism.

15. The filter of claim 14 wherein the retrieval interlocking mechanism is a retrieval hook.

16. The filter of claim 15 wherein a distal end of the elongated body extends beyond the distal ends of each of the second leg group legs in the filter-compressed configuration.

17. The filter of claim 16 further comprising a hook positioned at the distal end of the elongated body.

18. The filter of claim 17 wherein
    the second leg group comprises six legs,
    and
    the distal section includes six flanges configured to separate the hooks on the distal end of the second leg group legs in the filter-compressed configuration
    and
    the flanges lie approximately equidistant from each other.

19. The filter of claim 13 wherein a distal end of the elongated body extends beyond the distal ends of each of the second leg group legs in the filter-compressed configuration.

20. The filter of claim 19 further comprising a hook positioned at the distal end of the elongated body.

* * * * *